(12) United States Patent
Chiu

(10) Patent No.: US 8,481,699 B2
(45) Date of Patent: Jul. 9, 2013

(54) MULTIPLEX BARCODED PAIRED-END DITAG (MBPED) LIBRARY CONSTRUCTION FOR ULTRA HIGH THROUGHPUT SEQUENCING

(75) Inventor: Kuo Ping Chiu, Taipei (TW)

(73) Assignee: Academia Sinica, Taipei (TW)

( * ) Notice: Subject to any disclaimer, the term of this patent is extended or adjusted under 35 U.S.C. 154(b) by 700 days.

(21) Appl. No.: 12/610,749

(22) Filed: Nov. 2, 2009

(65) Prior Publication Data

US 2011/0015096 A1 Jan. 20, 2011

Related U.S. Application Data

(60) Provisional application No. 61/225,392, filed on Jul. 14, 2009.

(51) Int. Cl.
*C07H 21/00* (2006.01)
*G01N 33/487* (2006.01)

(52) U.S. Cl.
USPC .............................. 536/23.1; 702/20; 506/16

(58) Field of Classification Search
USPC ................................ 506/16; 702/20; 536/23.1
See application file for complete search history.

(56) References Cited

U.S. PATENT DOCUMENTS

2007/0238101 A1* 10/2007 Ruan et al. .................... 435/6

OTHER PUBLICATIONS

Yu et al., GenBank accession EF625819, Jun. 13, 2007.*
Shendure et al., Science, 2005, 309:1728-173).*
Shendure et al., Science, 2005, supplementary material.*
Strausberg et al., Nat. Rev. Genetics, 2003, 4:409-418.*
Acul NEB 2008.*
Mmel NEB 2008.*
Zhao et al., (2007) "Whole-GenomeMappingof HistoneH3Lys4and27 Trimethylations RevealsDistinctGenomic Compartments in Human Embryonic Stem Cells" Cell Stem Cell 1, 286-298.
Chiu et al., (2007) "Pathway aberrations of murine melanoma cells observed in Paired-End diTag transcriptomes" BMC Cancer 7:109.
Chiu et al. (2006) "PET-Tool: a software suite for comprehensive processing and managing of Paired-End diTag (PET) sequence data" BMC Bioinformatics 7:390.

(Continued)

*Primary Examiner* — Ardin Marschel
*Assistant Examiner* — Jeremy C Flinders
(74) *Attorney, Agent, or Firm* — Hsiu-Ming Saunders; Intellectual Property Connections, Inc.

(57) ABSTRACT

Multiplex barcoded Paired-End Ditag (mbPED) library construction for ultra high throughput sequencing is disclosed. The mbPED library comprises multiple types of barcoded Paired-End Ditag (bPED) nucleic acid fragment constructs, each of which comprises a unique barcoded adaptor, a first tag, and a second tag linked to the first tag via the barcoded adaptor. The two tags are the 5'- and 3'-ends of a nucleic acid molecule from which they originate. The barcoded adaptor comprises a barcode, a first polynucleotide sequence comprising a first restriction enzyme (RE) recognition site, and a second polynucleotide sequence comprising a second RE recognition site and covalently linked to the first polynucleotide sequence via the barcode. The two REs lead to cleavage of a nucleic acid at a defined distance from their recognition sites. The length of the adaptor is set so that the bPED nucleic acid fragment fits one-step sequencing.

17 Claims, 5 Drawing Sheets

OTHER PUBLICATIONS

The ENCODE Project Consortium "Identification and analysis of functional elements in 1% of the human genome by the ENCODE pilot project" NATURE vol. 447, Jun. 14, 2007, 799-816.

The FANTOM Consortium and RIKEN Genome Exploration Research Group and Genome Science Group (Genome Network Project Core Group) "The Transcriptional Landscape of the Mammalian Genome" Science vol. 309 Sep. 2, 2005 1559-1563.

Loh et al., "The Oct4 and Nanog transcription network regulates pluripotency in mouse embryonic stem cells" Nature Genetics vol. 38 No. 4 Apr. 2006 431-440.

Ng et al., "Gene identification signature (GIS) analysis for transcriptome characterization and genome annotation" Nature Methods vol. 2 No. 2 Feb. 2005, 105-111.

Ng et al., "Multiplex sequencing of paired-end ditags (MS-PET): a strategy for the ultra-high-throughput analysis of transcriptomes and genomes" Nucleic Acids Research, 2006, vol. 34, No. 12, e84.

Ng et al., "Paired-End diTagging for Transcriptome UNIT 21.12 and Genome Analysis" Curr. Protoc. Mol. Biol. 79:21.12.1-21.12.42. 2007 by John Wiley & Sons, Inc.

* cited by examiner

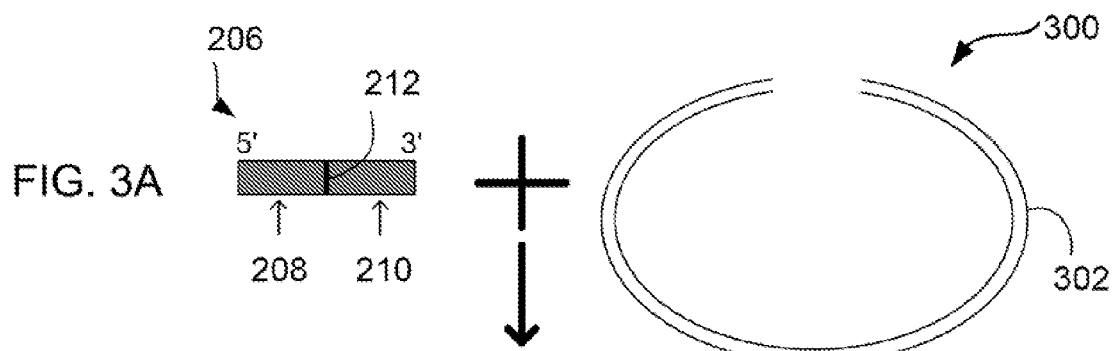
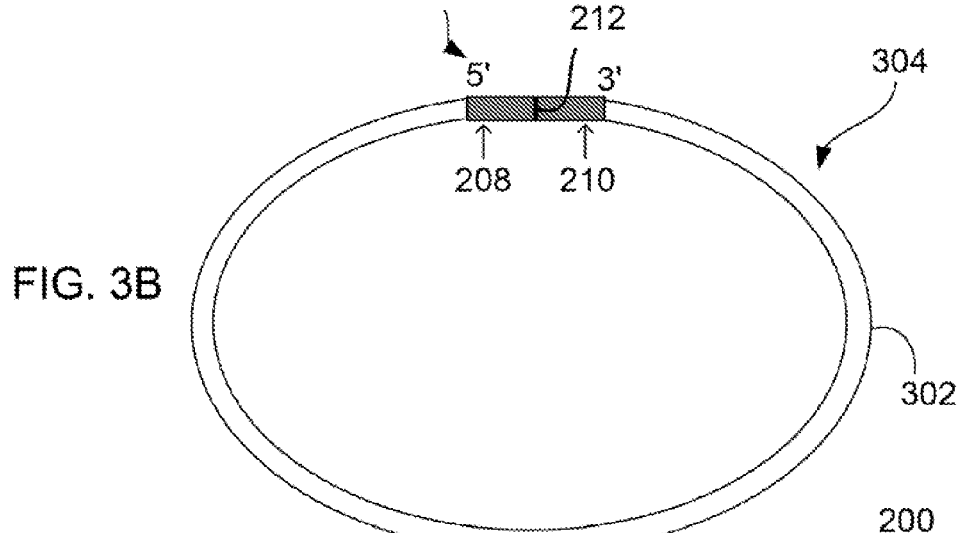
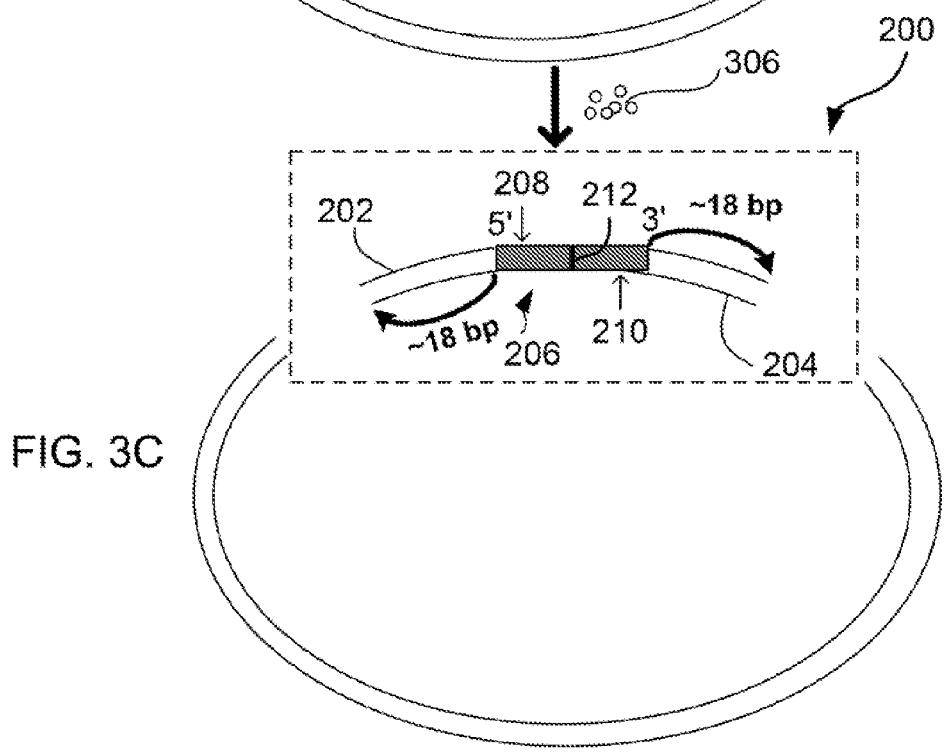
FIG. 3A
FIG. 3B
FIG. 3C

MULTIPLEX BARCODED PAIRED-END DITAG (MBPED) LIBRARY CONSTRUCTION FOR ULTRA HIGH THROUGHPUT SEQUENCING

REFERENCES TO RELATED APPLICATION

The present application claims priority to U.S. Provisional Application Ser. No. 61/725,392, filed Jul. 14, 2009, which is herein incorporated by reference in its entirety.

FIELD OF THE INVENTION

The present invention relates generally to the field of nucleic acid sequencing, including transcriptome sequencing, genome sequencing, and the assembly of the sequencing results into a contiguous sequence.

BACKGROUND OF THE INVENTION

Paired-End sequencing is a robust method for the study of gene expression and regulation. It links the 5' terminal tags (~18-20 bp each) of genomic DNA sequences or double stranded cDNA molecules directly to their corresponding 3' terminal tags in the same order and orientation for high throughput sequencing. In practice, the Paired-End approach has been routinely used as a wetlab procedure for making libraries either from double-stranded cDNA molecules, or genomic DNA fragments enriched by chromatin immunoprecipitation (ChIP). The biological meanings of the transcriptomic or genomic sequences are subsequently unraveled by sequencing and bioinformatics analyses. Some applications of this approach were demonstrated in previous work for the development of the Paired-End Ditagging (PET) technology.

Next-veneration sequencers, e.g., SOLiD™ 3 sequencers manufactured by Applied Biosystems (AB), Solexa sequencers by Illumina, and 454 sequencers by Roche, have incorporated the Paired-End sequencing as an intrinsic feature. Currently, the SOLiD™ 3 system runs on three types of libraries, namely fragment library, Mate-Paired (MP) library, and barcoded fragment library (See SOLiD™ 3 System Library Preparation Guide, page 1, which is herein incorporated by reference in its entirety). The construction of a Mate-Paired or a barcoded fragment library is more complex than that of a fragment library, and the cost for sequencing is also almost twice as much. Thus, a design to bypass the current protocol of making Mate-Paired library constructs is strongly desirable and would be beneficial for the scientific community.

Therefore, a heretofore unaddressed need exists in the art to address the aforementioned deficiencies and inadequacies, especially in connection with development of a simplified protocol for making Paired-End library constructs that can lower the cost and allow high throughput sequencing.

SUMMARY OF THE INVENTION

In one aspect, the invention relates to a barcoded adaptor that comprises:
(a) a barcode, comprising a virtual or a known nucleotide sequence;
(b) a 5'-flanking sequence, comprising a first restriction enzyme (RE) recognition site; and
(c) a 3'-flanking sequence, comprising a second RE recognition site, covalently linked to the 5'-flanking sequence via the barcode;

wherein the first and the second REs are the same or different and they each lead to cleavage of a nucleic acid at a defined distance from their respective recognition site.

In another aspect, the invention relates to a barcoded adaptor that consists of:
(a) a barcode, consisting of a virtual or a known nucleotide sequence;
(b) a 5'-flanking sequence, consisting of a first RE recognition site; and
(c) a 3'-flanking sequence, consisting of a second RE recognition site and covalently linked to the 5'-flanking sequence via the barcode;

wherein the first and the second REs are the same or different and they each lead to cleavage of a nucleic acid at a distance from their respective recognition site.

Further in another aspect, the invention relates to a barcoded Paired-End Ditag (bPED) nucleic acid fragment that comprises:
(a) a barcoded adaptor, comprising:
  (i) a barcode, comprising a virtual or a known nucleotide sequence;
  (ii) a 5'-flanking sequence, comprising a first RE recognition site; and
  (iii) a 3'-flanking sequence, comprising a second RE recognition site and covalently linked to the 5'-flanking sequence via the barcode;
  wherein the first and the second REs are the same or different and they each lead to cleavage of a nucleic acid sequence at a defined distance from their respective recognition sites;
(b) a first tag; and
(c) a second tag, covalently linked to the first tag via the barcoded adaptor;

wherein the first and the second tags are the 5'- and 3'-ends of a nucleic acid molecule from which the two tags originate, and wherein the length of the adaptor is adapted to allow the bPED nucleic acid fragment fits one-step sequencing.

Further in another aspect, the invention relates to a bPED nucleic acid fragment that consists of:
(a) a barcoded adaptor, consisting of:
  (i) a barcode, consisting of a virtual or a known nucleotide sequence
  (ii) a 5'-flanking sequence, consisting of a first RE recognition site; and
  (iii) a 3'-flanking sequence, consisting of a second RE recognition site and covalently linked to the 5'-flanking sequence via the barcode;
  wherein the first and the second REs are the same or different and they each lead to cleavage of a nucleic acid sequence at a defined distance from their respective recognition sites;
(b) a first tag; and
(c) a second tag, covalently linked to the first tag via the barcoded adaptor;

wherein the first and the second tags are the 5'- and 3'-ends of a nucleic acid molecule from which the two tags originate, and wherein the length of the adaptor is adapted to allow the length of the bPED nucleic acid fragment fits one-step sequencing.

In another aspect, the invention relates to a bPED nucleic acid fragment library, which comprises more than one bPED nucleic acid fragment construct as described above.

In another aspect, the invention relates to a method of generating a bPED nucleic acid fragment. The method comprises the steps of:
(a) labeling a nucleic acid molecule with a barcode by ligating the two ends of the nucleic acid molecule to a barcoded adaptor to obtain a circularized barcoded nucleic acid molecule, wherein the barcoded adaptor comprises:
  (i) a barcode, comprising a virtual or a real, known nucleotide sequence;
  (ii) a 5'-flanking sequence, comprising a first RE recognition site; and
  (iii) a 3'-flanking sequence, comprising a second RE recognition site;
  wherein the barcode is located in between the 5'- and 3'-flanking sequences, and the first and the second REs are the same or different and they each lead to cleavage of a nucleic acid at a defined distance from their respective recognition sites; and
  (b) digesting the circularized barcoded nucleic acid molecule with the first and second REs and lead to cleavage of the barcoded nucleic acid molecule, and thereby generating the bPED nucleic acid fragment.

Further in another aspect, the invention relates to a multiplex barcoded Paired-End Ditag (mbPED) DNA fragment library, in which the multiplex library comprises more than one bPED nucleic acid fragment library as aforementioned and the barcode of the more than one bPED nucleic acid fragment of each library is different.

Yet in another aspect, the invention relates to a method of constructing a bPED nucleic acid fragment library as aforementioned, which comprises the steps of:
  (a) providing a library comprising nucleic acid molecules;
  (b) labeling the library with a barcode by ligating the nucleic acid molecules to a barcoded adaptor to obtain barcoded nucleic acid molecules, wherein the barcoded adaptor comprises:
    (i) a barcode, comprising a virtual or a known nucleotide sequence;
    (ii) a 5'-flanking sequence, comprising a first RE recognition site; and
    (iii) a 3'-flanking sequence comprising a second RE recognition site;
    wherein the barcode is located in between the first and the second polynucleotide sequences, and the first and the second REs are the same or different and they each lead to cleavage of a nucleic acid at a defined distance from their respective recognition sites; and
  (c) digesting the barcoded nucleic acid molecules with the first and the second Res which bind to their respective recognition sites and lead to cleavage of the barcoded nucleic acid molecules, and thereby generating the bPED nucleic acid fragment library.

In one embodiment of the invention, the nucleic acid molecules may be selected from the group consisting of cDNA, chromatin immunoprecipitation fragments, and genomic nucleic acid fragments.

In another embodiment of the invention, the barcoded adaptor is free of the nucleotide sequence of SEQ ID NO: 2.

In another embodiment of the invention, the lengths of the tag 1 and tag 2 are no shorter than 14 bp.

In another embodiment of the invention, the first and/or the second REs each lead to cleavage of a nucleic acid at ≧14 or ≧18 bp away from their respective recognition sites.

In another embodiment of the invention, the RE recognition site is free of an EcoP15I site (SEQ ID NO: 1). The RE may be selected from the group consisting of MmeI, BpuEI, AcuI, and BsgI.

In another embodiment of the invention, the length of the barcoded adaptor is <20 bp.

Further in another embodiment of the invention, the length of the barcode is at least 3, 4 or 5 bp.

In another embodiment of the invention, the barcoded adaptor comprises the nucleotide sequence selected from the group consisting of SEQ ID NOs: 3-14. Alternatively, the barcoded adaptor may be selected from the group consisting of SEQ ID NOs: 3-14. The barcoded adaptor may consist of the nucleotide sequence selected from the group consisting of SEQ ID NOs: 3-14.

Yet in one embodiment of the invention, each bPED nucleic acid fragment in each library is attached to a solid support, e.g., a bead, inside a sequencer via a 5'-end adaptor comprising a primer site for a sequencing reaction such as P1 adaptor. Each bPED nucleic acid fragment of each library may further comprises a 3'-end adaptor such as P2 adaptor.

These and other aspects will become apparent from the following description of the preferred embodiment taken in conjunction with the following drawings, although variations and modifications therein may be affected without departing from the spirit and scope of the novel concepts of the disclosure.

The accompanying drawings illustrate one or more embodiments of the invention and, together with the written description, serve to explain the principles of the invention. Wherever possible, the same reference numbers are used throughout the drawings to refer to the same or like elements of an embodiment.

BRIEF DESCRIPTION OF THE DRAWINGS

FIGS. 3A-3C are schematic drawings showing steps for construction of a bPED nucleic acid fragment library.

DETAILED DESCRIPTION OF THE INVENTION

Definitions

Figure 1A:
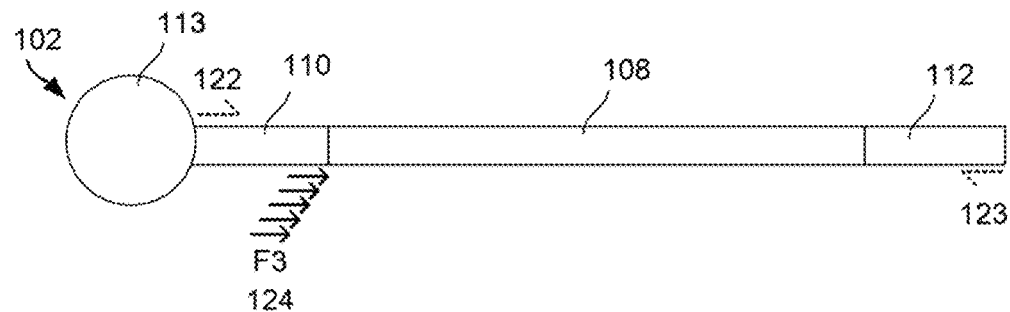
FIG. 1A is a schematic drawing showing a fragment library construct made for SOLiD™ 3 sequencing.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, "around", "about" or "approximately" shall generally mean within 20 percent, preferably within 10 percent, and more preferably within 5 percent of a given value or range. Numerical quantities given herein are approximate, meaning that the term "around", "about" or "approximately" can be inferred if not expressly stated.

As used herein, "barcode" shall generally mean a virtual or a known nucleotide sequence that is used as a fingerprint for labeling a DNA fragment and/or a library and for constructing a multiplex library. The library includes, but not limited to, genomic DNA library, cDNA library and ChIP library. Libraries, of which each is separately labeled with a distinct barcode, may be pooled together to form a multiplex barcoded library for performing sequencing simultaneously, in which each barcode is sequenced together with its flanking tags located in the same construct and thereby serves as a fingerprint for the DNA fragment and/or library labeled by it. A "barcode" is positioned in between two restriction enzyme (RE) recognition sequences. A barcode may be virtual, in which case the two RE recognition sites themselves become a barcode. Preferably, a barcode is made with a specific nucleotide sequence having 1, 2, 3, 4, 5, 6, or more base pairs in length. The length of a barcode may be increased along with the maximum sequencing length of a sequencer. For example, the current SOLiD™ 3 sequencer can only sequence up to 50 bp of DNA constructs, thus the length of a barcode for making bPED should take into account the current limitation that bPED sequences are limited to 50 bp. If a SOLiD™ machine can sequence longer than 50 bp someday, the barcode length may be increased accordingly.

As used herein, "virtual" shall generally mean not in actual form but existing or resulting in effect.

As used herein, "fingerprint" shall generally mean a distinctive or identifying mark or characteristic.

As used herein, "restriction enzyme recognition site" and "restriction enzyme binding site" are interchangeable. The terms "barcoded adaptor" and "barcoded adaptor sequence" are interchangeable. The terms "barcode" and "barcode sequence" are interchangeable.

As used herein, "one-step sequencing" means sequencing that requires only one set of primers. Sequencing of a Mate-Paired (MP) library with a SOLiD™ 3 sequencer requires two primer sets, the R3 set and the F3 set. Each set requires 5 primers to completely sequence a tag (e.g., the F3 set for Tag 1 of Mate Pair, the R3 set for Tag 2 of Mate Pair). Thus, two sequencing reactions, one for the R3 set, the other for the F3 set, are needed in sequencing an MP library. With the barcoded PED technology of the invention, only the F3 set of primers is required for completely sequencing the paired tags (Ditag).

Invention Distinguished from Prior Art

Figure 1B:
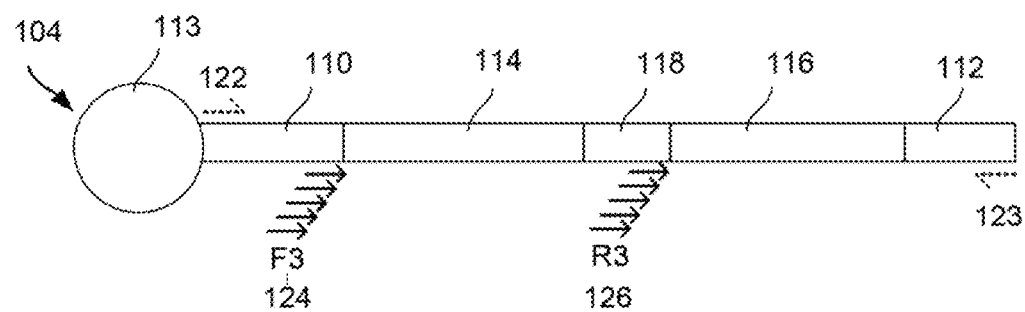
FIG. 1B is a schematic drawing showing a Mate-Paired library construct made for SOLiD™ 3 sequencing.
Figure 1C:
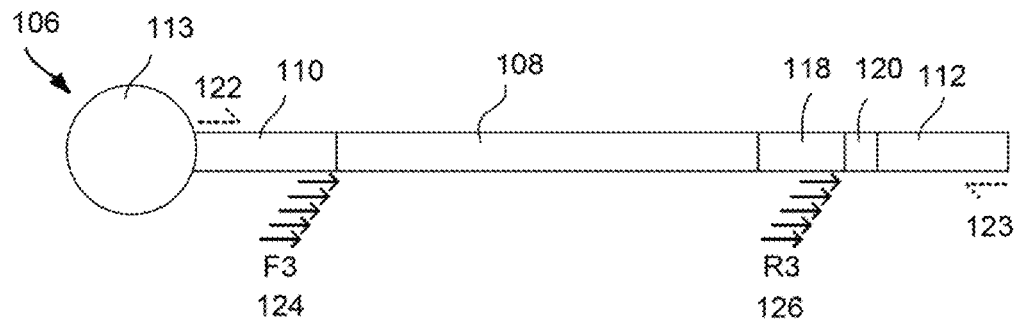
FIG. 1C is a schematic drawing showing a barcoded fragment library construct made for SOLID™ 3 sequencing.

FIGS. 1A-1C show prior art sequencing library constructs currently run by a SOLID™ 3 sequencer. As designed by Applied Biosystems Inc., the current SOLID™ machine runs on three types of library constructs: fragment library construct 102, Mate-Paired library construct 104, and barcoded fragment library construct 106. These three types of library constructs have four features in common: 1) each has a magnetic bead 113, a P1 adaptor 110, and a P2 adaptor 112; 2) the P1 adaptor 110 comprises a nucleotide sequence that has an annealing site for an outbound PCR primer 122 near the end attached to the bead 113; 3) the P1 adaptors 110 also comprises a nucleotide sequence that has annealing sites for annealing with a set of sequencing primers, F3 set, 124 near the central DNA fragment; 4) the P2 adaptor 112 comprises a nucleotide sequence that has an annealing site for an inbound PCR primer 123 near the bead-free end oldie P2 adaptor 112. The inbound PCR primer 123 of the P2 adaptor 112 is to be used together with the outbound PCR primer 122 of the P1 adaptor 110 for PCR, including emulsion PCR, amplifications.

The fragment library construct 102 has only one insert, i.e., a DNA fragment 108 (FIG. 1A). DNA fragments 108 used in a fragment library 102 are normally prepared by sonication. The DNA fragment 108 is attached to P1-coupled bead 102 via P1 adaptor 110. Prior to sequencing, emulsion PCR is used to make tens of thousands of copies of the same construct attaching to the bead 113 using the PCR primer pair 122 and 123 located in the P1 and P2 adaptors in the opposite direction. After emulsion PCR, P1-coupled beads 113 with PCR products are enriched with large polystyrene beads coated with P2 adaptor 112, which is followed by centrifugation in a glycerol gradient to separate the captured beads with templates from the beads without templates. In the SOLID™ 3 sequencer, the P1 adaptor 110 comprises annealing sites for the F3 primer set 124 and can sequence the DNA fragment 108 up to 50 bp.

A Mate-Paired library consists of a pair of DNA fragments that are "Mates" because they originated from the two ends of the same piece of DNA (e.g., genomic DNA and/or transcriptomic DNAs). As shown in FIG. 1B, each Mate-Paired construct 104 contains two inserts, called Tag 1 114 and Tag 2 116, which originate from the terminal sequences of a DNA molecule, A Mate-Paired library construct 104 is generated as follows: each DNA fragment of ~0.8 to ~6 Kb is ligated to two CAP regions 118 (one for each end) and then to an internal adaptor, which links the CAP sequences and thus circularize the whole construct "CAP-insert-CAP" molecule. The CAP region comprises an EcoP15I recognition sequence (CTGCT-GTAC; SEQ ID NO: 1), and the internal adaptor comprises the sequence of SEQ ID NO: 2 (CGTACATCCGCCTTGGC-CGT). The circularized DNA is digested with EcoP15I or by nick translation to obtain Mate-Paired DNA fragments, which are ligated to P1 and P2 to generate Mate-Paired construct 104. In the Mate-Paired library constructs, both P1 adaptor 110 and internal adaptor-CAP region 118 have sequencing primer annealing sites F3 124 and R3 126 and each allows sequencing of up to 50 bp of Tag 1 114 and Tag 2 116, respectively, A barcoded fragment library 106 is prepared by directly ligating DNA fragments 108 to P1 adaptor 110 and a hybrid adaptor 118, 120, 112 that contains an internal adaptor-CAP region 118, a barcode sequence 120, and a P2 adaptor 112. A barcoded fragment construct 106 is very similar to a Mate-Paired construct 104 in the sense that both contain two unknown regions that need to be sequenced. However, each barcoded fragment construct 106 contains only one piece of library-originated DNA fragment 108, located in the upstream of the template, which is to be sequenced together with the commercialized barcode sequence 120. Unlike the barcoded Paired-End Ditag approach disclosed in the present invention, the barcode sequence 120 in the barcoded fragment construct 106 has no functional or direct physical association with the library-originated DNA fragment 108. The P1 adaptor 110 has annealing sites for the F3 primer set 124, which can sequence up to 50 bp of the DNA fragment 108. The internal adaptor-CAP region 118 has the annealing site for the R3 primer set 126, which can sequence 5 bp of the barcode 120. In other words, the barcode and the target DNA are sequenced in two separate reads. To completely sequence Mate-Paired and barcoded fragment library constructs, the R3 primer set 126 located in the internal adaptor-CAP region 118 is used in the first sequencing reaction, and the F3 primer set 124 located at the P1 adaptor 110 is used in the second sequence reaction.

The barcoded Paired-End Ditag (bPED) technology of the invention is distinct from the Mate-Paired method at least in terms of the purpose, length/structure, strategy and simplicity.

(1) Purpose: The Mate-Paired method utilizes an internal adaptor-CAP region for a different purpose. The internal adaptor-CAP region is used for circularization of genomic fragments and purification. The Mate-Paired method simply has no barcode sequence for labeling any DNA fragment or any library. By contrast, the barcode sequence of the invention is for labeling a DNA fragment and/or a library.

(2) Length and structure: The length of the internal adaptor-CAP region is about 20 bp in size. The barcode of the invention may be as short as only a few by in size, or as a virtual barcode.

(3) Strategy: The Mate-Paired method uses the internal adaptor-CAP region and a restriction enzyme to create a construct that has to be sequenced by two-step sequencing with two sets of primers. In contrast, the invention uses a barcoded adaptor to create a construct that requires only one-step sequencing with a single set of primers. In other words, unlike a Mate-Paired library, the barcode and the two tags of a bPED DNA fragment are sequenced as one read, rather than being sequenced as two separate reads.

(4) Simplicity: The Mate-Paired method is tedious. In contrast, the bPED method of the invention is simple, straightforward and fast.

Figure 2A:
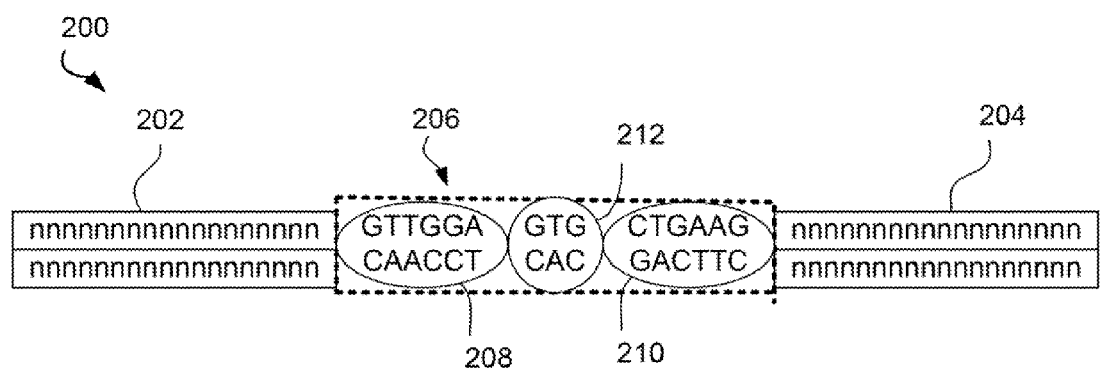
FIG. 2A is a schematic drawing illustrating a barcoded Paired-End Ditag (bPED) DNA construct according to one embodiment of the invention.

A Paired-End Ditag method was previously disclosed, in which two MmeI recognition sites in an adaptor ligated to both ends of a DNA insert were used to cut out two tag sequences (each tag ~18-20 bp) from the terminal ends of the insert for high throughput sequencing. That method differs from the present invention at least in two aspects. Firstly, it did not utilize a barcode in the library and each library had to be sequenced separately. Secondly, a Paired-End Ditag construct has two restriction enzyme sites located at the two ends of a DNA insert, whereas the barcoded Paired-End Ditag molecular construct 200 (FIG. 2A) and bPED sequencing library construct containing the barcoded Paired-End Ditag molecular construct 200 (FIG. 2B) of the invention have two restriction enzyme sites 208, 210 positioned in between two DNA tags 202, 204.

Although the Applied Biosystem's SOLID™ 3 System is among the best of ultra high throughput sequencers in the world, protocols used by the machine are not yet very sophisticated. The same issue applies to all other next-generation sequencers. According to the current SOLID™ 3 protocols, the fragment library 102 is made from short (~100 bp) DNA fragments 108 generated by sonication; the Mate-Pair library 104 is constructed with a much more complicated procedure involving circularization of a DNA insert followed by EcoP15I digestion or nick translation of the circularized DNA; and the barcoded fragment library 106 is generated with a procedure distinct from the bPED approach disclosed here. Procedures for constructing the Mate Pair 104 and barcoded fragment 106 libraries are not only tedious and tricky, but also reagent-consuming and cost-ineffective, making it unaffordable for small laboratories. Conversely, the bPED approach of the invention directly ligates the barcoded adaptor 206 to the insert 302 (FIGS. 3A and 3B), followed by enzymatic digestion to generate barcoded Paired-End Ditag (bPED) structure in a single fragment 200 (FIG. 3C).

The above-mentioned limitations for the Paired-End Ditag, technology and next-generation sequencers can be further solved by using the multiplex barcoded Paired-End Ditag (mbPED) strategy 400 (FIGS. 3A-3C and 4) disclosed in the application. The invention can become a superior method for genomic investigations.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

Structures of Barcoded Adaptors and Barcoded Paired-End Ditags (bPEDs)

The invention relates to designing a set of barcoded adaptors and employing type II restriction enzymes (either the same or different species) that bind their recognition sites within the barcoded adaptors to generate bPEDs in a one-barcode-per-library fashion to construct bPED libraries from genomic and/or transcriptomic libraries. The bPED constructs (FIGS. 2-3) are then used to make "fragment" libraries for ultra high throughput sequencing. The "DNA fragment 108" in the fragment library 102 (FIG. 1) is replaced by the bPED construct 200 (FIG. 2). Thus, the barcode sequence 212 not only has a direct physical association with the restriction enzyme sites 208, 210 and the ditag sequences 202, 204, it also functions as an intrinsic fingerprint to represent the ditag sequences 202, 204, which are retrieved from the terminal ends of a DNA insert.

FIG. 2 illustrates the structural relationship between the barcode 212, barcoded adaptor 206, and barcoded Ditag 200. The barcoded adaptor 206, which has an internal barcode sequence 212 (which can be of variable sequence and length) and two flanking type II restriction enzyme (RE) recognition sites 208, 210 (which can be of the same or different species), is used for bPED library construction. As shown in FIGS. 3A-3C, a bPED fragment 200, ~50 bp in size, is generated by ligation of a barcoded adaptor 206 of a known sequence with a DNA fragment 302 in a library, followed by restriction enzyme digestion 306, which leading to cleavage of two terminal tags 202, 204 of the insert 302 at a defined distance from the barcoded adaptor's RE recognition sites 208, 210.

Example 2

Barcoded Paired-End Ditag (bPED) Library

FIGS. 3A-3C show steps for construction of a bPED library 300. Barcoded Paired-End Ditags (bPEDs) 200 are generated from a barcoded adaptor 206 that has a barcode sequence 212 (either a virtual or a real sequence) flanked by a pair of type II restriction enzyme recognition sites 208, 210. The barcoded adaptor 206 is ligated to DNA fragments (inserts) 302. Digestion of the ligated DNA fragments 304 by REs 306, which binds to the RE recognition sites 208, 210, releases two terminal tag sequences 202, 204 from the insert 302 and thus generates a bPED fragment 200.

Example 3

Figure 2B:
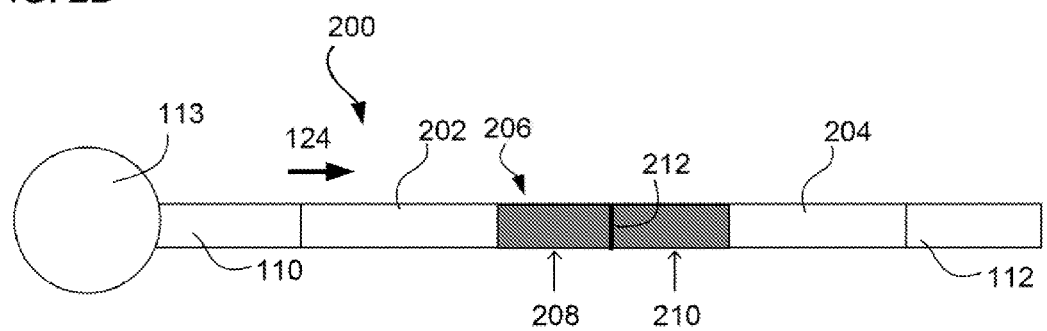
FIG. 2B is a schematic drawing illustrating a bPED nucleic acid fragment library construct made for SOLiD™ 3 sequencing.

Using Mono-Barcoded Paired-End Ditag Library as a Fragment Library for Sequencing Using SOLID™ 3 sequencing as an example, each individual bPED library or multiplex barcoded Paired-End Ditag (mbPED) library can be treated as a single "fragment" library for a SOLID™ 3 sequencer, i.e., each bPED clone is treated as a single DNA fragment during library construction, sequencing, and sequence analysis by bioinformatics means. In such an application, the DNA fragment 108 between P1 and P2 adaptors 110, 112 of a fragment library 102 (FIG. 1A) is replaced by a bPED sequence 200 (FIG. 2B) generated from a barcoded adaptor 206 containing a pair of type II. RE recognition sites 208, 210 (FIG. 2B).

Example 4

Figure 4:
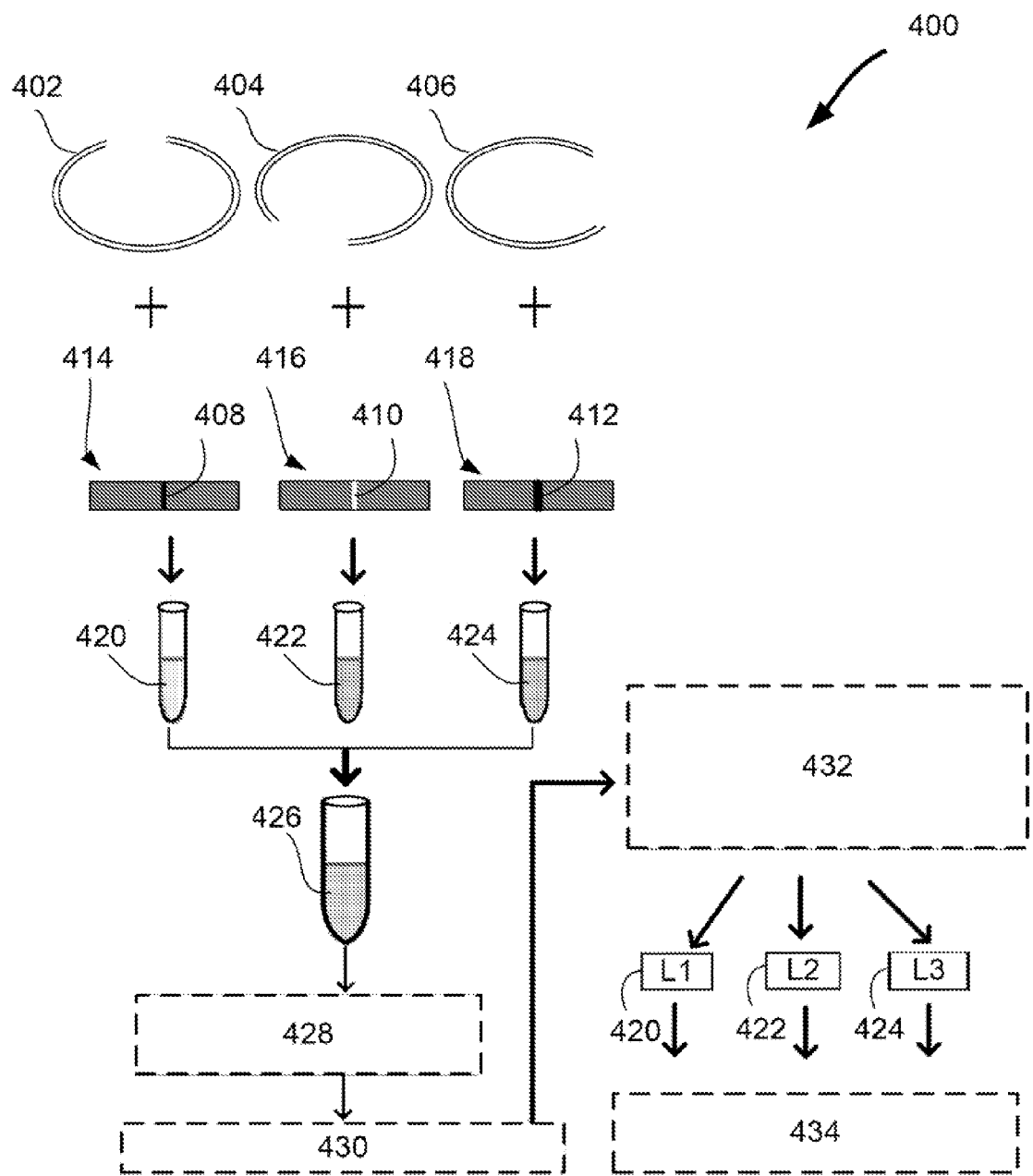
FIG. 4 is a schematic drawing showing steps for construction of an mbPED-ChIP library and data processing.

Multiplex Barcoded Paired-End Ditag (mbPED) Library Enables Sequencing Multiple Libraries Simultaneously The invention allows us to prepare individual barcoded libraries, each associated with a particular barcode fingerprint. Such bPED libraries can be sequenced and analyzed individually, or to simplify a wetlab procedure, they can be mixed together to form a multiplex barcoded Paired-End Ditag (mbPED) library and then sequenced as one (FIG. 4). A sequencer will sequence through the whole barcoded Paired-End Ditag region, and prior to sequence data analysis and comparison, libraries can be distinguished on the basis of their unique barcode fingerprints.

FIG. 4 illustrates steps for construction of an mbPED-ChIP library and data processing 400. Multiple types of chromatin-immunoprecipitation (ChIP) fragment libraries, e.g., ChIP library #1 fragment 402, ChIP library #2 fragment 404, and ChIP library #3 fragment 406, are used as starting materials. During the ligation step, each barcode is associated with a particular type of ChIP library. Thus, the barcode #1 408, the barcode #2 410, and the barcode #3 412 are physically linked to the ChIP library #1 fragment 402, ChIP library #2 fragment 404, and ChIP library #3 fragment 406 via the barcode #1-generated adaptor 414, barcode #2-generated adaptor 416, and barcode #3-generated adaptor 418, respectively. Various ChIP library preparations 420, 422, 424 are subsequently mixed together to form a mega-library 426, which can be treated as a single library to save reagents and to simplify the process of library manipulation. The multiplex library 426 continues through all wetlab procedures 428. When a SOLID™ 3 sequencer is used, the multiplex library 426 can be sequenced just like sequencing a single fragment library 430. Afterwards, through sequence data analysis by bioinformatics approaches 432, the barcode #1 408, the barcode #2 410, and the barcode #3 412, which are sequenced together with Ditags, can be used to group the Ditags into their corresponding ChIP libraries L1 420, L2 422 and L3 424. Each library then continues through independent analysis 434.

One of the most evident advantages of the barcoded Paired-End Ditag approach is that multiple libraries can be mixed together to form an mbPED library for concurrent sequencing and data analysis, and each internal barcode sequence, together with the flanking type II RE recognition sites, can act as an intrinsic fingerprint to associate Ditag sequences to a particular cellular origin (e.g., cancer cells, normal cells, or a single cell) or to a specific biological entity (e.g., ChIP fragments bound by a specific transcription factor).

Example 5

Applications of bPEDs to all Next-Generation Sequencing Platforms

The bPED approach can be used to make libraries for all types of next-generation sequencers, including SOLID™, Solexa Sequencer, and 454 Sequencing™, because of its powerful capability and simplicity resulted from utilization of barcoded bi-directional tag cutters. Barcoded Paired-End Ditags generated can be directly used to make sequencing libraries for both SOLID™ and Solexa sequencers. Because the sequencing length of a 454 sequencer can reach a few hundred base pairs, a procedure for making concatemers from bPEDs or mbPED may be used for 454 Sequencing™ so as to make such sequencing more cost-effective.

The advantages of the novel bPED cloning strategy are evident. To fully appreciate those advantages, it helps to define "sequencing workflow" as the overall process from off-instrument library preparation till the completion of on-instrument sequencing. These advantages include the following: 1) The mbPED approach allows us to combine the advantages of both Mate-Paired and fragment libraries; 2) The experimental procedure for Paired-End-mediated investigations can be significantly shortened and simplified by the mbPED approach; 3) Sequencing running costs can be cut in half; 4) Sequencing time can be reduced to half as well; 5) The mbPED approach allows multiple libraries to be prepared and analyzed in parallel so as to reduce bias that may result from separate library preparations and processing; 6) It will increase mappable ratio so as to increase data reliability and reproducibility, etc.

Example 6

Validation of Barcoded Adaptor Constructs Using pBluescript II KS(+) as a DNA Insert A large number of barcoded adaptors were generated by linking a variety of barcodes of variable lengths and sequences to homo- or hetero-restriction enzyme recognition sequences. They were evaluated for ligation and digestion efficiencies. Table 1 lists the selected barcoded adaptor candidates and their corresponding sequences. The symbol "BC" at the "construct" column stands for "barcode," the sequence of which is shown in the lower case at the "nucleotide sequence" column.

TABLE 1

Barcoded Adaptor

| Name | Construct | Nucleotide sequence | SEQ ID NO. |
|---|---|---|---|
| MM5 | MmeI-5bpBC-MmeI | 5'- GTTGGAgagtcTCCAAC -3' | 3 |
| MBp3 | MmeI-3bpBC-BpuEI | 5'- GTTGGAgtgCTTGAG -3' | 4 |
| BpBp3BpuEI-3bpBC-BpuEI | | 5'- CTCAAGgtgCTTGAG -3' | 5 |
| BpBp3BpuEI-3bpBC-BpuEI | | 5'- CTCAAGgtgCTTGAG -3' | 5 |
| mA3 | MmeI-3bpBC-AcuI | 5'- GTTGGAgtgCTGAAG -3' | 6 |
| ABp3 | AcuI-3bpBC-BpuEI | 5'- CTTCAGgtgCTTGAG -3' | 7 |
| MA5 | MmeI-5bpBC-AcuI | 5'- GTTGGAgagtcCTGAAG -3' | 8 |
| MBp5 | MmeI-5bpBC-BpuEI | 5'- GTTGGAgagtcCTTGAG -3' | 9 |
| MBs5 | MmeI-5bpBC-BsgI | 5'- GTTGGAgagtcGTGCAG -3' | 10 |
| AA5 | AcuI-5bpBC-AcuI | 5'- CTTCAGgagtcCTGAAG -3' | 11 |
| ABp5 | AcuI-5bpBC-BpuEI | 5'- CTT CAGgagtcCTTGAG -3' | 12 |
| ABs5 | AcuI-5bpBC-BsgI | 5'- CTTCAGgagtcGTGCAG -3' | 13 |
| BsBs5BsgI-5bpBC-BsgI | | 5'- CTGCACgagtcGTGCAG -3' | 14 |

During the initial screening, it was necessary to balance between the maximum sequencing length (which is ~50 bp) for the SOLID™ 3 sequencer currently used in the lab and the minimum tag length required for reliable mapping (which is ≧14 bp). A construct with a length longer than 50 bp would not be fully sequenced by the machine. On the other hand, a short tag of a construct is not sufficient for reliable mapping. Thus, only those restriction enzymes that lead to cleavage of a DNA at least 14-16 bp away from the recognition site were chosen. On the list shown in Table 1, all the REs, except MmeI, lead to cleavage of a DNA at 14-16 bp away from the recognition sites. MmeI leads to a cleavage of a DNA at 18-20 bp away and is the restriction enzyme selected for further experiments.

Figure 5:
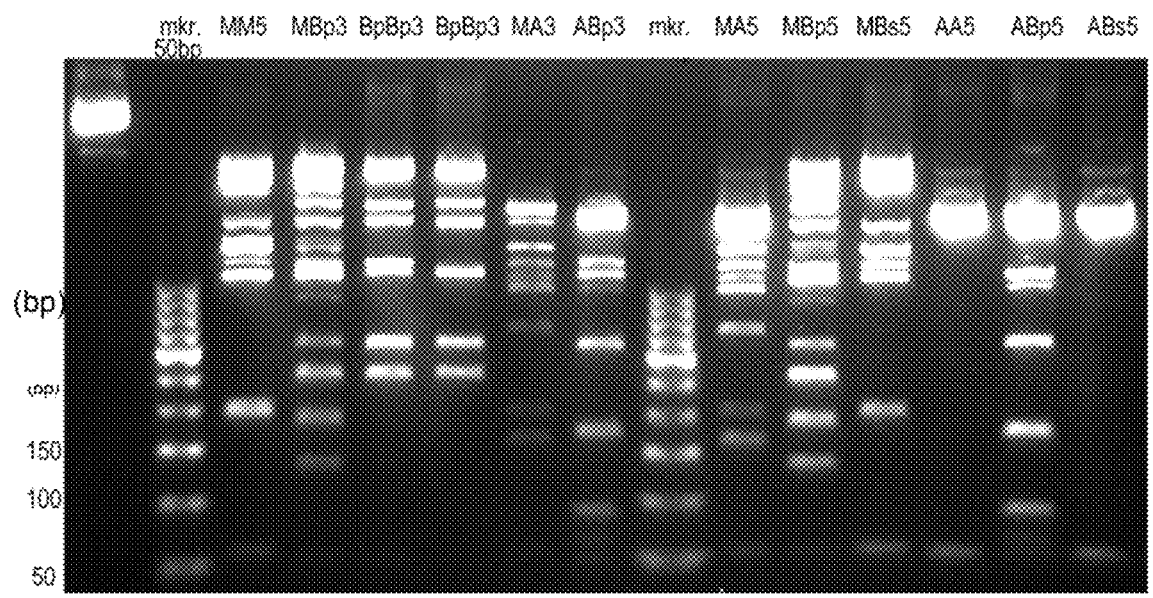
FIG. 5 is a photograph of an electrophoresis gel showing validation of various constructs of barcoded adaptors by restriction enzyme digestions of plasmid constructs. Each of the plasmid constructs contains a specific barcoded adaptor inserted into a pBluescript II KS(+) plasmid. The ~50 bp bands shown in the gel contain bPED, which comprises a barcoded adaptor and two tags that flank the barcoded adaptor. The intensity of the ~50 bp band indicates the efficacy of the corresponding barcoded adaptor.

The barcoded adaptors were ligated to pBluescript II KS(+) plasmid. Enzymatic digestions were carried out to validate the barcoded adaptors selected from initial screening. Clones containing single adaptors, as confirmed by sequencing, were selected and digested with their corresponding enzyme(s) for 6 hrs at 37° C. with a one-step procedure prior to agarose gel electrophoresis. Generation of a specific ~50 bp fragment was adopted as the criterion for the validation. FIG. 5 shows the results of validation of the constructs of barcoded adaptors. The sequence of ~50 bp fragments produced from various enzymatic digestions were confirmed by a PRIZM 3730 sequencer to ensure the fidelity of the validation.

It was found that both the RE combination and the "length" of the internal barcode have a significant impact on the efficiency of specific bPED production, while the "sequence" (or content) of the barcode has relatively insignificant influence. Constrained by the limitations mentioned above, however, the length of the barcode region can only be chosen between about 3 to about 5 bp, which in fact by itself is large enough for making tens of libraries simultaneously. The RE sequence can be used as a barcode as well. In general, an adaptor having a barcode of 5 bp sequence performs better than that having a 3 bp-barcode. The barcoded adaptor MM5, which contains a pair of MmeI recognition sites flanking a barcode sequence of 5 bp in length, was chosen as the primary candidate for further validation.

Thus, by using a pBluescript II KS(+) vector, which represents an uniformed insert, it was demonstrated that barcoded Paired-End Ditag (bPED) libraries could be generated by various combinations of RE sites and barcodes. The successful results paved the way toward further validation using random genomic sequences, which can be generated from sonication (or by a shotgun method), as inserts to better represent the real experimental conditions.

Example 7

Validation of Genomic Barcoded Paired-End Ditag Library

Since bPED libraries could be generated with certain barcoded adaptors from the vector pBluescript II KS(+), which consists of an invariable sequence, the next question would be whether a bPED library could be generated from a population of genomic shotgun sequences, which by nature consists of variable sequences and lengths. This question was tested on the shotgun sequences of HCT116 cancer genome as follows.

The barcoded adaptor MM5 was chosen in the study to constrict a genomic barcoded Paired-End Ditag, (bPED) library. The feasibility of using the barcoded adaptor MM5 (top strand: 5'-GTTGGAgagtcTCCAAC-3'; SEQ ID NO: 3) to make bPEDs from randomly sheared genomic sequences was tested by using HCT116 genomic shotgun fragments as the inserts. The adaptor MM5 was ligated to shotgun fragments of HCT116 genome to obtain bPEDs, which were then ligated to P1 and P2 adaptors. The presence of the barcoded adaptor MM5 in the bPEDs was validated by PCR using a barcoded adaptor-specific primer together with a P1 adaptor's primer.

Figure 6:
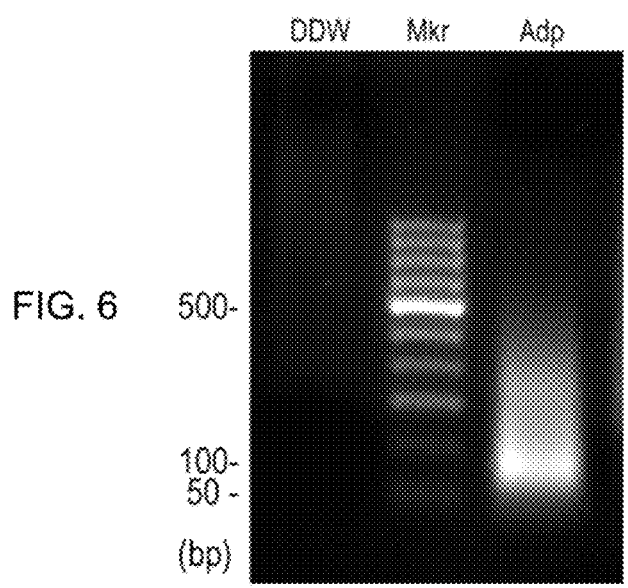
FIG. 6 is a photograph of an electrophoresis gel showing PCR validation of a bPED nucleic acid fragment library generated from randomly sheared HCT116 cancer genomic fragments.

FIG. 6 shows the results of PCR validation of a genomic barcoded Paired-End Ditag (bPED) library constructed with the barcoded adaptor MM5. Lane DDW: Negative control containing double distilled water instead of HCT116 genomic DNA fragments during ligation. Lane Mkr: Double-stranded DNA markers with sizes labeled in the left-hand side. Lane Adp: The HCT116 genome was isolated and fragmented by sonication to ~800 bp to ~2 Kb. The sonicated fragments were ligated to the double-stranded barcoded adaptor MM5, which was followed by digestion with MmeI to generate a barcoded Paired-End Ditag (bPED) library. The bPED library was then ligated to P1 and P2 adaptors, which are used for SOLID™ 3 fragment library preparation, and amplified by 20 cycles of PCR reactions using a minus strand of MM5 and P1 adaptor sequences as a primer pair.

The result has demonstrated the feasibility of using barcoded adaptors as designed in making bPED libraries. Conceivably, mbPED analyses can be conducted by simply mixing different bPED libraries, which contain different barcode sequences.

The invention has a great potential for commercial applications, not only for the SOLID™ system, but also for the Solexa and 454 systems. The most evident benefits include a near 50% reduction in the running costs, protocol simplification, sequencer running time reduction, an increase in instrument sales, and most importantly, the mbPED strategy will create a new paradigm towards multi-dimensional investigations.

Sequencing Running Cost Reduction

The cost of running a current SOLID™ 3 sequencer remains high, although seemingly cheaper than Solexa and 454. As stated above, the SOLID™ 3 runs on three types of libraries: fragment library, Mate-Pair library, and barcoded fragment library. Among these libraries, the fragment library has the lowest running cost (~NT $300,000 or ~US $9,258 per slide per run) because only one DNA fragment in each template needs to be sequenced, while the running cost (~NT $530,000 or ~US $16,357 per slide per run) for the Mate-Pair and barcoded fragment libraries almost double that of the fragment library because two tags in each template need to be sequenced. Here, the bPED or mbPED libraries can be made offline (i.e., without using costly reagents for the library construction) and converted into fragment libraries for SOLID™ 3 sequencing. By doing so, the running cost can be cut almost in half.

Protocol Simplification and Sequencing Run Time Reduction

The cloning of bPEDs is accomplished prior to the construction of a sequencing library, so the procedure is more flexible and less stressful. Moreover, after the construction of bPEDs, the bPEDs from different libraries can be mixed together to form an mbPED library and be made into a single fragment library for sequencing. This will not only save cost, but also simplify the procedure and shorten sequencer running time. Those sequences with the same barcode fingerprint can be grouped back to re-generate individual libraries.

Acquiring the Multiplex Barcoded Paired-End Ditag (mbPED) Technology Will Promote Instrument Sales The competition for the sales of next-generation sequencers, especially between SOLID™ and Solexa, is incredibly high. While the success of a sale heavily relies on the capability of a sequencer and the versatility of its protocol and applications, incorporating the barcoded ditag cloning strategy of the present invention will provide a new momentum for instrument sale.

Multiplex Barcoded Paired-End Ditag (mbPED) Approach Will Create a New Paradigm Enabling Effective Multi-Aspect Investigations Current wetlab methodologies are limited to a one-library-one-biological-aspect manner. With the barcoded ditag approach, multiple barcoded Paired-End Ditag libraries can be mixed together to form a single library. Such a single library, which virtually contains multiple biological aspects, can be processed as one, until individual libraries need to be separated again for cross-library comparisons. For example, cells of different types (e.g. cancer vs. normal), cells taken from different time points or with different treatments can be pooled together after being labeled with different barcodes. Although such a library is physically considered as a single library, it is virtually generated from multiple libraries. Processing such a library will reduce the bias that may otherwise result from processing those multiple libraries separately. This approach will also reduce the cost and save manpower.

All of the references cited herein are incorporated by reference in their entirety.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments and examples were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference.

What is claimed is:

1. An isolated barcoded Paired-End Ditag (bPED) nucleic acid fragment, comprising:
   (a) a barcoded adaptor, comprising:
      (i) a barcode, comprising at least one base pair of a known nucleotide sequence;
      (ii) a 5'-flanking sequence, comprising a first restriction enzyme (RE) recognition site; and
      (iii) a 3-flanking sequence, comprising a second RE recognition site and covalently linked to the 5'-flanking sequence via the barcode;

wherein the length of the barcoded adaptor is 18 or fewer base pairs, and the first and the second REs are the same or different and they each allow binding of specific restriction enzymes that lead to cleavage of a nucleic acid sequence at a defined distance from their respective recognition sites;
(b) a first tag; and
(c) a second tag, covalently linked to the first tag via the barcoded adaptor;
wherein the first tag corresponds to the 5'-end of a nucleic acid molecule, and the second tag corresponds to the 3'-end of the nucleic acid molecule, and the sequence of the nucleic acid molecule is unknown.

2. The isolated bPED nucleic acid fragment of claim 1, wherein the lengths of the first and the second tags are no shorter than 14 bp.

3. The isolated bPED nucleic acid fragment of claim 1, wherein the barcoded adaptor consists of:
(a) the barcode;
(b) the 5 flanking sequence, consisting of the first RE recognition site; and
(c) the 3-flanking sequence, consisting of the second RE recognition site.

4. The isolated bPED nucleic acid fragment of claim 1, wherein the first and the second restriction enzyme recognition sites allow binding of specific restriction enzymes that lead to cleavage of a nucleic acid at $\geq 14$ away from their respective recognition sites.

5. The isolated bPED nucleic acid fragment of claim 1, wherein the length of the barcode is no shorter than 3 bp.

6. The isolated bPED nucleic acid fragment of claim 1, wherein the first RE and/or the second RE are selected from the group consisting of MmeI, BpuEI, AcuI, and BsgI.

7. The isolated bPED nucleic acid fragment of claim 1, wherein the barcoded adaptor comprises the nucleotide sequence selected from the group consisting of SEQ ID NOs: 3-14.

8. The isolated bPED nucleic acid fragment of claim 1, wherein the barcoded adaptor consists of a nucleotide sequence selected from the group consisting of SEQ ID NOs: 3-14.

9. A method of generating the isolated bPED nucleic acid fragment of claim 1, comprising the steps of:
(a) labeling a nucleic acid molecule of unknown sequence with a barcode by ligating the two ends of the nucleic acid molecule to a barcoded adaptor to obtain a circularized barcoded nucleic acid molecule, wherein the barcoded adaptor comprises:
(i) a barcode, comprising at least one base pair of a known nucleotide sequence;
(ii) a 5'-flanking sequence, comprising a first RE recognition site; and
(iii) a 3'-flanking sequence, comprising a second RE recognition site and covalently linked to the 5% flanking sequence via the barcode;
wherein the length of the barcoded adaptor is 18 or fewer base pairs, and the first and the second REs are the same or different and they allow binding of specific restriction enzymes that lead to cleavage of a nucleic acid at a defined distance from their respective recognition sites; and
(b) digesting the circularized barcoded nucleic acid molecule with the first and second REs and lead to cleavage of the circularized barcoded nucleic acid molecule, and thereby generating the bPED nucleic acid fragment.

10. An isolated barcoded Paired-End Ditag (bPED) nucleic acid fragment, consisting of:
(a) a barcoded adaptor, consisting of:
(i) a barcode, consisting of at least one base pair of a known nucleotide sequence;
(ii) a 5'-flanking sequence, consisting of a first restriction enzyme (RE) recognition site; and
(iii) a 3'-flanking sequence, consisting of a second restriction enzyme (RE) site and covalently linked to the 5-flanking sequence via the barcode;
wherein the length of the barcoded adaptor is 18 or fewer base pairs, and the first and the second REs are the same or different and they each allow binding of specific restriction enzymes that lead to cleavage of a nucleic acid sequence at a defined distance from their respective recognition sites;
(b) a first tag; and
(c) a second tag, covalently linked to the first tag via the barcoded adaptor;
wherein the first tag corresponds to the 5'-end of a nucleic acid molecule, and the second tag corresponds to the 3'-end of the nucleic acid molecule, and the sequence of the nucleic acid molecule is unknown.

11. The isolated bPED nucleic acid fragment of claim 1, wherein the nucleic acid molecule is selected from the group consisting of cDNA, chromatin immunoprecipitation fragments, and genomic nucleic acid fragments.

12. The isolated bPED nucleic acid fragment of claim 10, wherein the first and/or the second REs each lead to cleavage of a nucleic acid at $\geq 14$ bp away from their respective recognition sites.

13. The isolated bPED nucleic acid fragment of claim 1, wherein the nucleic acid molecule originates from a cancer cell, a normal cell or a single cell.

14. The isolated bPED nucleic acid fragment of claim 1, wherein the first and the second REs are the same.

15. The isolated bPED nucleic acid fragment of claim 1, wherein the nucleic acid molecule originates from a cancer cell.

16. The isolated bPED nucleic acid fragment of claim 10, wherein the nucleic acid molecule is selected from the group consisting of cDNA, chromatin immunoprecipitation fragments, and genomic nucleic acid fragments.

17. The isolated bPED nucleic acid fragment of claim 10, wherein the nucleic acid molecule originates from a cancer cell, a normal cell or a single cell.

* * * * *

SEQUENCE LISTING

```
<160> NUMBER OF SEQ ID NOS: 14

<210> SEQ ID NO 1
<211> LENGTH: 9
<212> TYPE: DNA
<213> ORGANISM: Artificial Sequence
<220> FEATURE:
<223> OTHER INFORMATION: EcoP15I recognition sequence

<400> SEQUENCE: 1 ctgctgtac                                                            9

<210> SEQ ID NO 2
<211> LENGTH: 20
<212> TYPE: DNA
<213> ORGANISM: Artificial Sequence
<220> FEATURE:
<223> OTHER INFORMATION: Mate-Paired contruct Internal adaptor sequence
```

-continued

<400> SEQUENCE: 2
cgtacatccg ccttggccgt                                              20

<210> SEQ ID NO 3
<211> LENGTH: 17
<212> TYPE: DNA
<213> ORGANISM: Artificial Sequence
<220> FEATURE:
<223> OTHER INFORMATION: MM5: MmeI-5bpBC- MmeI

<400> SEQUENCE: 3
gttggagagt ctccaac                                                 17

<210> SEQ ID NO 4
<211> LENGTH: 15
<212> TYPE: DNA
<213> ORGANISM: Artificial Sequence
<220> FEATURE:
<223> OTHER INFORMATION: MBp3: MmeI-3bpBC-BpuEI

<400> SEQUENCE: 4
gttggagtgc ttgag                                                   15

<210> SEQ ID NO 5
<211> LENGTH: 15
<212> TYPE: DNA
<213> ORGANISM: Artificial Sequence
<220> FEATURE:
<223> OTHER INFORMATION: BpBp3: BpuEI-3bpBC-BpuEI

<400> SEQUENCE: 5
ctcaaggtgc ttgag                                                   15

<210> SEQ ID NO 6
<211> LENGTH: 15
<212> TYPE: DNA
<213> ORGANISM: Artificial Sequence
<220> FEATURE:
<223> OTHER INFORMATION: MA3: MmeI-3bpBC-AcuI

<400> SEQUENCE: 6
gttggagtgc tgaag                                                   15

<210> SEQ ID NO 7
<211> LENGTH: 15
<212> TYPE: DNA
<213> ORGANISM: Artificial Sequence
<220> FEATURE:
<223> OTHER INFORMATION: ABp3: AcuI-3bpBC-BpuEI

<400> SEQUENCE: 7
cttcaggtgc ttgag                                                   15

<210> SEQ ID NO 8
<211> LENGTH: 17
<212> TYPE: DNA
<213> ORGANISM: Artificial Sequence
<220> FEATURE:
<223> OTHER INFORMATION: MA5: MmeI -5bpBC-AcuI

<400> SEQUENCE: 8
gttggagagt cctgaag                                                 17

<210> SEQ ID NO 9
<211> LENGTH: 17

```
<212> TYPE: DNA
<213> ORGANISM: Artificial Sequence
<220> FEATURE:
<223> OTHER INFORMATION: MBp5: MmeI -5bpBC-BpuEI

<400> SEQUENCE: 9
gttggagagt ccttgag                                                  17

<210> SEQ ID NO 10
<211> LENGTH: 17
<212> TYPE: DNA
<213> ORGANISM: Artificial Sequence
<220> FEATURE:
<223> OTHER INFORMATION: MBs5: MmeI -5bpBC-BpuEI

<400> SEQUENCE: 10
gttggagagt cgtgcag                                                  17

<210> SEQ ID NO 11
<211> LENGTH: 17
<212> TYPE: DNA
<213> ORGANISM: Artificial Sequence
<220> FEATURE:
<223> OTHER INFORMATION: AA5: AcuI-5bpBC-AcuI

<400> SEQUENCE: 11
cttcaggagt cctgaag                                                  17

<210> SEQ ID NO 12
<211> LENGTH: 17
<212> TYPE: DNA
<213> ORGANISM: Artificial Sequence
<220> FEATURE:
<223> OTHER INFORMATION: ABp5: AcuI-5bpBC-BpuEI

<400> SEQUENCE: 12
cttcaggagt ccttgag                                                  17

<210> SEQ ID NO 13
<211> LENGTH: 17
<212> TYPE: DNA
<213> ORGANISM: Artificial Sequence
<220> FEATURE:
<223> OTHER INFORMATION: ABs5: AcuI-5bpBC-BsgI

<400> SEQUENCE: 13
cttcaggagt cgtgcag                                                  17

<210> SEQ ID NO 14
<211> LENGTH: 17
<212> TYPE: DNA
<213> ORGANISM: Artificial Sequence
<220> FEATURE:
<223> OTHER INFORMATION: BsBs5: BsgI-5bpBC-BsgI

<400> SEQUENCE: 14
ctgcacgagt cgtgcag                                                  17
```